(12) United States Patent
Fukazawa et al.

(10) Patent No.: US 7,330,042 B2
(45) Date of Patent: Feb. 12, 2008

(54) SUBSTRATE INSPECTION SYSTEM, SUBSTRATE INSPECTION METHOD, AND SUBSTRATE INSPECTION APPARATUS

(75) Inventors: Kazuhiko Fukazawa, Misato (JP); Yasuto Kawashima, Fujisawa (JP)

(73) Assignee: Nikon Corporation, Tokyo (JP)

( * ) Notice: Subject to any disclaimer, the term of this patent is extended or adjusted under 35 U.S.C. 154(b) by 295 days.

(21) Appl. No.: 10/807,262

(22) Filed: Mar. 24, 2004

(65) Prior Publication Data

US 2005/0072945 A1   Apr. 7, 2005

(30) Foreign Application Priority Data

Mar. 26, 2003  (JP)  ............... 2003-084741

(51) Int. Cl.
  *G01R 31/28*  (2006.01)
  *G01N 21/88*  (2006.01)
  *G06K 9/00*  (2006.01)
(52) U.S. Cl. .............. 324/765; 250/559.44; 356/237.5; 382/149
(58) Field of Classification Search ...................... None
  See application file for complete search history.

(56) References Cited

U.S. PATENT DOCUMENTS 4,644,172 A  *  2/1987  Sandland et al. ........... 250/548
5,699,447 A  *  12/1997  Alumot et al. .............. 382/145
6,452,671 B1 *  9/2002  Uda et al. .................. 356/237.2
6,790,287 B2 *  9/2004  Shiga et al. ................. 118/719
6,818,459 B2 *  11/2004  Wack et al. .................. 438/14
6,891,627 B1 *  5/2005  Levy et al. .................. 356/625

FOREIGN PATENT DOCUMENTS

| JP | A 11-072443 | 3/1999 |
| JP | A 2000-035319 | 2/2000 |
| JP | A 2001-099788 | 4/2001 |
| JP | A 2002-076077 | 3/2002 |

* cited by examiner

*Primary Examiner*—Ernest Karlsen
(74) *Attorney, Agent, or Firm*—Oliff & Berridge, PLC

(57) ABSTRACT

It is an object of the present invention to provide a substrate inspection system, a substrate inspection method, and a substrate inspection apparatus for realizing efficient operation of inspecting both a large region and a small region of a substrate. The present invention includes a first inspection apparatus 11 executing a macro inspection of each of a plurality of substrates 14(*l*) to 14(*n*) and outputting information on presence/absence of a defect on each of the substrates; a storage unit 12 storing therein the information on presence/absence of a defect outputted from the first inspection apparatus for each of the substrates; and a second inspection apparatus 13 executing an inspection of a predetermined portion of the substrate. The second inspection apparatus refers to the presence/absence information stored in the storage unit, and inspects a substrate, the one without a defect, of the plural substrates 14(*l*) to 14(*n*).

6 Claims, 7 Drawing Sheets

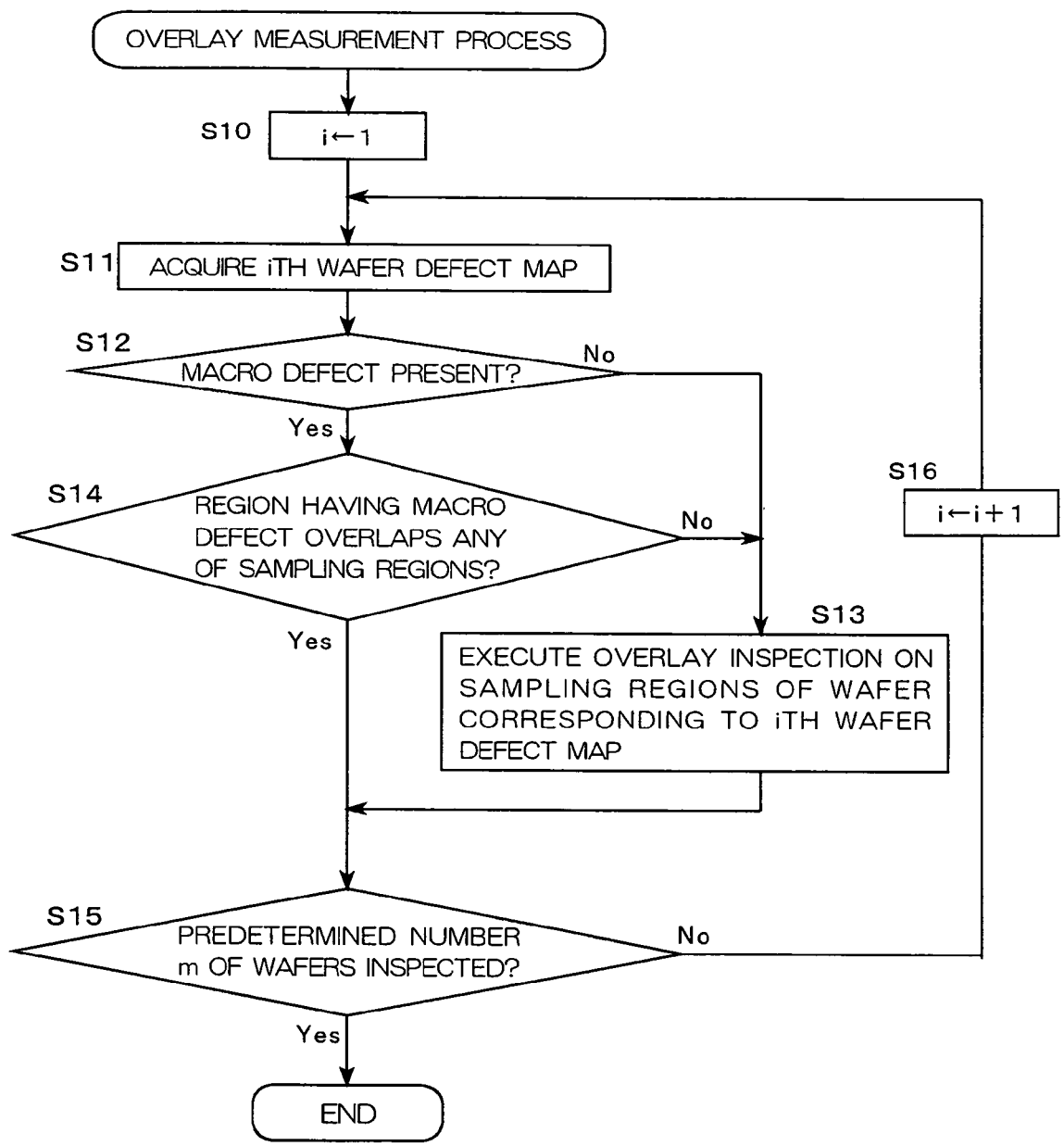

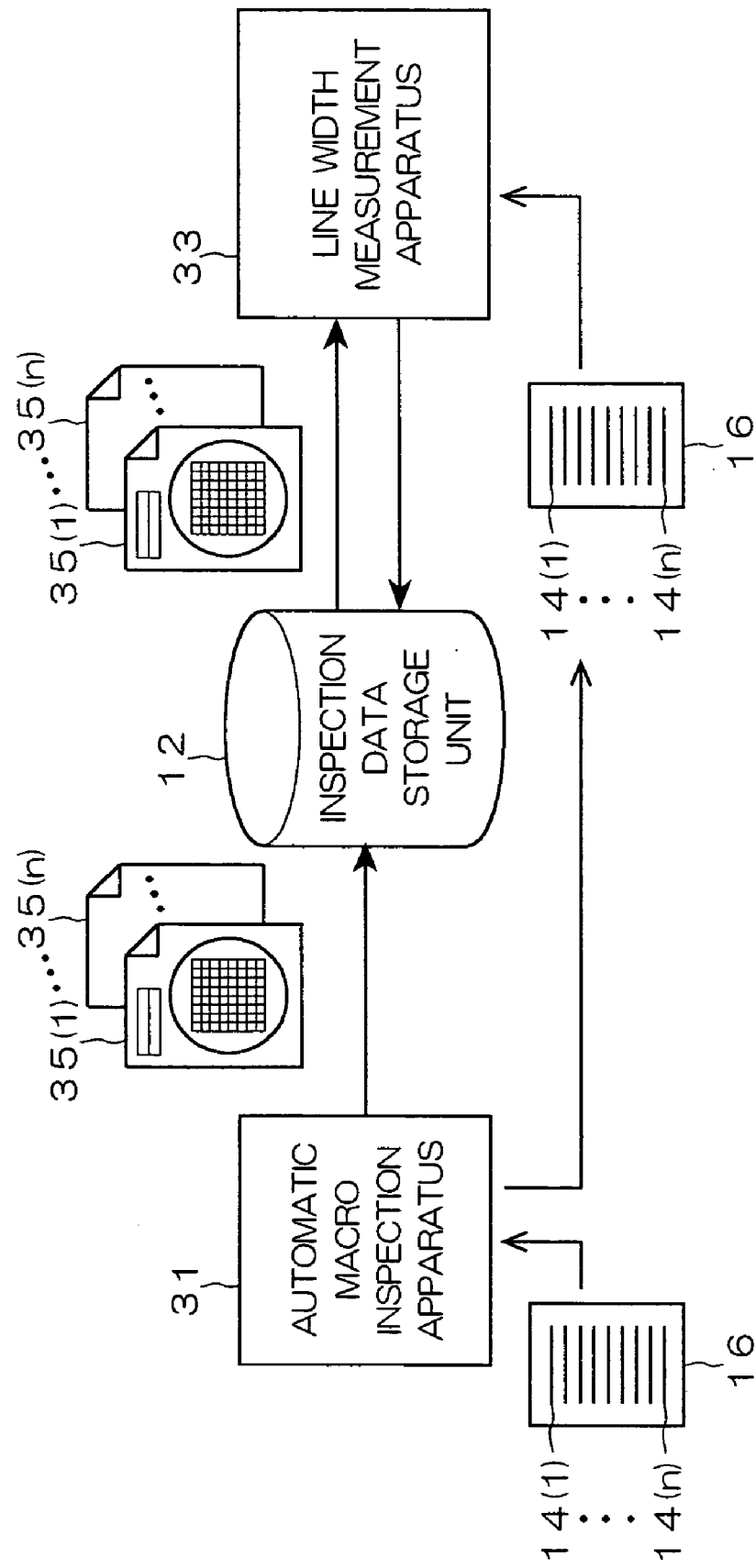

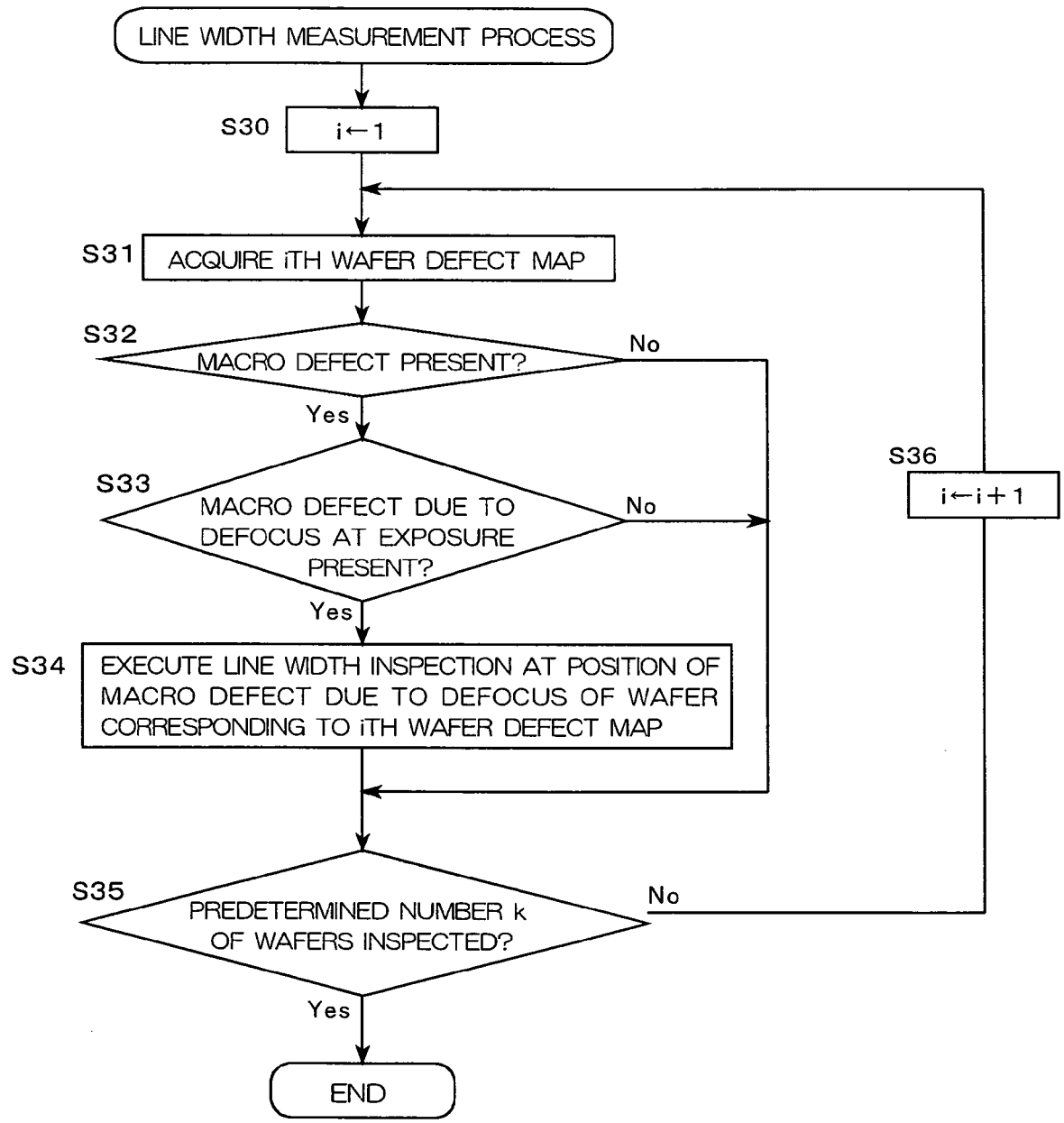

SUBSTRATE INSPECTION SYSTEM, SUBSTRATE INSPECTION METHOD, AND SUBSTRATE INSPECTION APPARATUS

BACKGROUND OF THE INVENTION

1. Field of the Invention

The present invention relates to a substrate inspection system, a substrate inspection method, and a substrate inspection apparatus for inspecting substrates in the manufacturing process of semiconductor circuit elements and of liquid crystal display elements, and more particularly, to a substrate inspection system, a substrate inspection method, and a substrate inspection apparatus suitable for the inspection after a lithographic process.

2. Description of the Related Art

Conventionally, in the manufacturing process of semiconductor circuit elements and liquid crystal display elements, substrates (wafers for IC manufacturing, glass substrates for liquid crystal manufacturing, and so on) are inspected in various ways in order to monitor over-time variations, and to detect reworkable defective products and remove nonreworkable defective products.

The various inspections made in the manufacturing process are mainly classified into a macro inspection and a micro inspection. The macro inspection and micro inspection greatly differ in the area ratio of a region to be inspected in a substrate and the entire substrate (an inspection area ratio), and also in the size of an object to be inspected and in required inspection accuracy.

The inspection area ratio in the macro inspection is 4% to 100%, and the size of an object to be inspected is several 100 µm or larger. That is, the macro inspection is for inspecting a large region for macroscopic defects visible to the human eye (for example, a foreign particle, a scratch on a resist pattern, and so on). On the other hand, in the micro inspection the inspection area ratio is about $10^{-8}$%, and inspection accuracy is 100 nm to 10 nm or less. In other words, the micro inspection is for inspecting an ultrasmall region for microscopic defects invisible to the human eye (for example, anomalies in line width of a resist pattern and so on).

Therefore, the macro inspection has been executed for large-range inspection on a substrate and the micro inspection has been executed for detailed inspection of a substrate, taking advantage of their merits. For example, Japanese Unexamined Patent Application Publication No. 2002-76077 discloses apparatus for executing macro inspection and micro inspection separately.

In view of realizing a single substrate inspection system to combine separate inspections of both of the regions, separately inspecting large and small regions of a substrate in the prior art described above, however, is not always an efficient way to operate the system.

SUMMARY OF THE INVENTION

It is an object of the present invention to provide a system, a method, and an apparatus for substrate inspection, for realizing an efficient operation of inspecting a large region and a small region of a substrate.

A substrate inspection system of the present invention includes: a first inspection apparatus executing a macro inspection of each of a plurality of substrates and outputting information on presence/absence of defect(s) on each of the substrates; a storage unit storing therein the information on presence/absence of defect(s) outputted from the first inspection apparatus for each of the substrates; and a second inspection apparatus executing an inspection of predetermined portion(s) of the substrate. The second inspection apparatus refers to the information on presence/absence of defect(s) stored in the storage unit and executes the inspection of substrate(s) of the plural substrates which does/do not have the defect(s).

It is preferable that the second inspection apparatus in the above-described substrate inspection system executes the inspection by measuring a relative offset between resist pattern(s) formed on a surface of the substrate and underlying pattern(s).

Another substrate inspection system of the present invention includes: a first inspection apparatus executing a macro inspection of each of a plurality of substrates and outputting information on distribution of defect(s) on each of the substrates; a storage unit storing the information on distribution of defect(s) outputted from the first inspection apparatus for each of the substrates; and a second inspection apparatus executing an inspection of predetermined portion(s) of the substrate. The second inspection apparatus refers to the information on distribution of defect(s) stored in the storage unit and executes the inspection of substrate(s) of the plural substrates which does/do not have defect(s) distributed in the predetermined portion(s).

Preferably, the second inspection apparatus in this inspection system executes the inspection by measuring a relative offset between resist pattern(s)formed on a surface of the substrate and underlying pattern(s).

Still another substrate inspection system of the present invention includes: a first inspection apparatus executing a macro inspection of each of a plurality of substrates and outputting information on distribution and classification of defect(s) on each of the substrates; a storage unit storing therein the information on distribution and classification of defect(s) outputted from the first inspection apparatus for each of the substrates; and a second inspection apparatus executing an inspection of predetermined portion(s) of the substrate. The second inspection apparatus refers to the information on distribution and classification of defect(s) stored in the storage unit and determines substrate(s) to be inspected from the plural substrates.

Preferably, the second inspection apparatus in the above-described substrate inspection system determines substrate(s) to be inspected according to how much kind(s) of the defect(s) contained in the classification information is/are associated with kind(s) of defect(s) detectable by said second inspection apparatus.

Preferably, the second inspection apparatus in the above-described substrate inspection system executes the inspection by measuring a line width of resist pattern(s) formed on a surface of the substrate.

A substrate inspection method of the present invention includes: a first inspection step of executing a macro inspection of each of a plurality of substrates and outputting information on presence/absence of defect(s) on each of the substrates; a storage step of storing the information on presence/absence of defect(s) outputted in the first inspection step for each of the substrates; and a second inspection step of executing an inspection of predetermined portion(s) of the substrate. In the second inspection step, the information on presence/absence of defect(s) stored in the storage step is referred to, and the inspection is executed on substrate(s) of the plural substrates that does/do not have the defect(s).

Preferably, in the second inspection step of the above-described substrate inspection method, the inspection is executed by measuring a relative offset between resist pattern(s) formed on a surface of the substrate and underlying pattern(s).

Another substrate inspection method of the present invention includes: a first inspection step of executing a macro inspection of each of a plurality of substrates and outputting information on distribution of defect(s) on each of the substrates; a storage step of storing the information on distribution of defect(s) outputted in the first inspection step for each of the substrates; and a second inspection step of executing an inspection of predetermined portion(s) of the substrate. In the second inspection step, the information on distribution of defect(s) stored in the storage step is referred to, and the inspection is executed on substrate(s) of the plural substrates that does/do not have the defect(s) distributed in the predetermined portion(s).

Preferably, in the second inspection step of the above-described inspection method, the inspection is executed by measuring a relative offset between resist pattern(s) formed on a surface of the substrate and underlying pattern(s).

Still another substrate inspection method of the present invention includes: a first inspection step of executing a macro inspection of each of a plurality of substrates and outputting information on distribution and classification of defect(s) on each of the substrates; a storage step of storing the information on distribution and classification of defect(s) outputted in the first inspection step for each of the substrates; and a second inspection step of executing an inspection of predetermined portion(s) of the substrate. In the second inspection step, the information on distribution and classification of defect(s) stored in the storage step is referred to, and substrate(s) to be inspected is/are determined from the plural substrates.

Preferably, in the second inspection step of the above-described substrate inspection method, substrate(s) to be inspected is/are determined according to how much kind(s) of the defect(s) contained in the classification information is/are associated with kind(s) of defect(s) detectable in the second inspection step.

Preferably, in the second inspection step of the above-described substrate inspection method, the inspection is executed by measuring a line width of resist pattern(s) formed on a surface of the substrate.

A substrate inspection apparatus of the present invention includes: a storage unit storing therein information on presence/absence of defect(s) on each of a plurality of substrates, the information on presence/absence of defect(s) being obtained as a result of a macro inspection of each of the substrates; and an inspection section executing an inspection of predetermined portion(s) of the substrate. The inspection section executes the inspection of substrate(s) of the plural substrates which does/do not have the defect(s), based on the information on presence/absence of defect(s) stored in the storage unit.

Another substrate inspection apparatus of the present invention includes: a storage unit storing therein information on distribution of defect(s) on each of a plurality of substrates, the information on distribution of defect(s) being obtained as a result of a macro inspection of each of the substrates; and an inspection section executing an inspection of predetermined portion(s) of the substrate. The inspection section executes the inspection of substrate(s) of the plural substrates which does/do not have the defect(s) distributed in the predetermined portion(s), based on the information on distribution of defect(s) stored in the storage unit.

Still another substrate inspection apparatus of the present invention includes: a storage unit storing therein information on distribution and classification of defect(s) on each of a plurality of substrates, the information on distribution and classification of defect(s) being obtained as a result of a macro inspection of each of the plural substrates; and an inspection section executing an inspection of predetermined portion(s) of the substrate.

The inspection section determines substrate(s) to be inspected from the plural substrates based on the information on distribution and classification of defect(s) stored in the storage unit.

BRIEF DESCRIPTION OF THE DRAWINGS

FIG. 3A illustrates pre-set sampling regions 13a;
FIG. 3B illustrates an example where a region in which the macro defect 14a(j) is distributed overlaps the sampling region 13a;
FIG. 3C illustrates an example where the region in which the macro defect 14a(j) is distributed does not overlap any of the sampling regions 13a;
FIG. 4 is a flowchart showing a concrete example of overlay measurement process;
FIG. 5 is a block diagram showing the configuration of a substrate inspection system 30 of a second embodiment;
FIG. 7 is a flowchart showing a concrete example of line width measurement process.

DESCRIPTION OF THE PREFERRED EMBODIMENTS

Hereinafter, embodiments of the present invention will be explained in detail using the drawings.

First Embodiment

Figure 1:
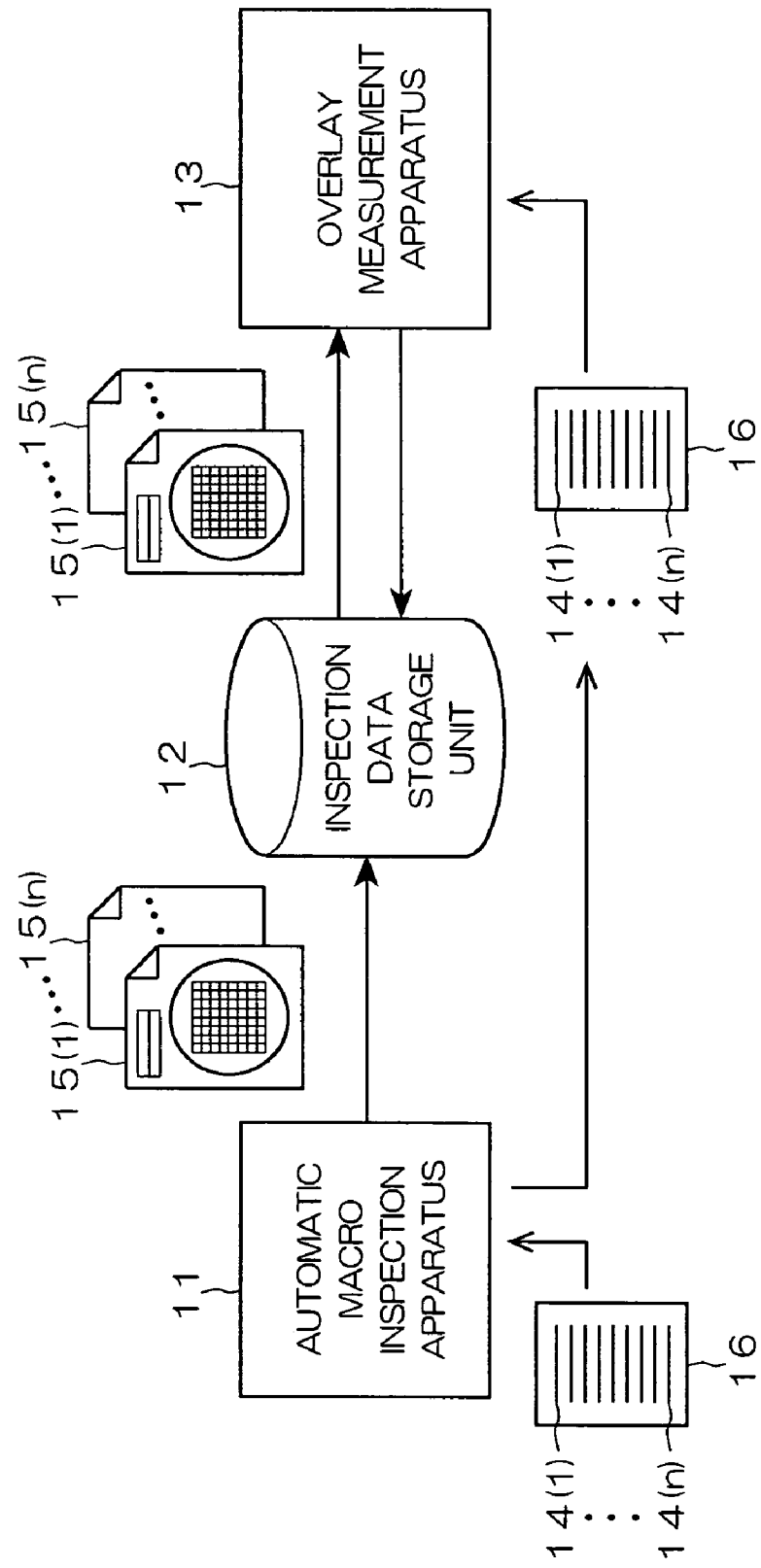
FIG. 1 is a block diagram showing the configuration of a substrate inspection system 10 of a first embodiment.

As shown in FIG. 1, a substrate inspection system 10 of a first embodiment is constituted of an automatic macro inspection apparatus 11, an inspection data storage unit 12, and an overlay measurement apparatus 13. The automatic macro inspection apparatus 11 and the inspection data storage unit 12 are connected to each other via a not-shown communication means, and similarly the inspection data storage unit 12 and the overlay measurement apparatus 13 are connected to each other via a not-shown communication means, so that the entire system constitutes a network.

In the manufacturing process of semiconductor circuit elements, this substrate inspection system 10 executes a macro inspection and an overlay inspection on wafers 14(l) to 14(n) for IC manufacturing in order to monitor over-time variation, and to detect reworkable defective products and eliminate nonreworkable defective products (to be described in detail later).

The wafers 14(l) to 14(n) to be inspected (substrates to undergo inspection) are horizontally housed in one cassette 16 and arranged in a vertical direction. Here, the wafers are designated with the reference codes 14(l) to 14(n) in order, starting from one on the top tier to one on the bottom tier. "n" is an integer equal to 2 or more (for example, 25). Further, the wafers 14(l) to 14(n) here has already undergone a lithographic process.

Note that in the lithographic process, resist layers are coated on the surfaces of the wafers 14(l) to 14(n). Then, each of the resist layers is exposed to a circuit pattern of a mask (reticle) to develop exposed portions or unexposed portions thereof. Thus, the wafers 14(*l*) to 14(*n*) after the lithographic process have resist patterns formed on the surfaces thereof.

In the substrate inspection system 10, the wafers 14(*l*) to 14(*n*) stored in the cassette 16, which has the resist patterns on their surfaces thereof through the lithographic process, are first transferred to the automatic macro inspection apparatus 11 (a first inspection apparatus) by not-shown transfer means, and subsequently to the overlay measurement apparatus 13 (a second inspection apparatus).

The automatic macro inspection apparatus 11, which will be described in detail later, executes a macro inspection of each of the wafers 14(*l*) to 14(*n*). The overlay measurement apparatus 13 executes an overlay inspection on sampling regions of the wafers 14(*l*) to 14(*n*). In other words, in the substrate inspection system 10 the inspection of a large region (macro inspection) is executed first and the inspection of a small region (overlay inspection) is executed next.

Upon transfer of the cassette 16, the automatic macro inspection apparatus 11 and the overlay measurement apparatus 13 extract a wafer 14(*j*) (j=1 to n) one by one from the cassette 16 for predetermined inspections. Then, they put back the wafer 14(*j*) into the cassette 16 upon completion of the inspection.

The automatic macro inspection apparatus 11 illuminates a large region of the arbitrary wafer 14(*j*) of the wafers 14(*l*) to 14(*n*) and captures an image of the wafer 14(*j*) according to diffracted light and reflected light therefrom (disclosed in, for example, Japanese Unexamined Patent Application Publication No. Hei 11-72443). Then, the automatic macro inspection apparatus 11 automatically detects a macro defect 14*a*(*j*) on the wafer 14(*j*) (FIG. 2) by performing image processing on the obtained wafer image and monitoring a light intensity of the wafer image. An inspection area ratio of the automatic macro inspection apparatus 11 is 4% to 100%.

The macro defect 14*a*(*j*) detected by the automatic macro inspection apparatus 11 can be a foreign particle adhering to the surface of the wafer 14(*j*), a scratch on the resist pattern, unevenness of coating on the resist layer, unevenness of thickness, anomaly in cross-sectional shape due to defocus by exposure, or the like. In other words, the macro defect 14*a*(*j*) is a macroscopic defect visible to the human naked eye (several 100 μm or larger in size).

Further, the automatic macro inspection apparatus 11 automatically converts distribution information on the macro defect 14*a*(*j*) detected from the wafer 14(*j*) to electronic information to create a macro defect map 15(*j*) for automatic output. The macro defect map 15(*j*) contains information on the position coordinates and area of the detected macro defect 14*a*(*j*) on the wafer 14(*j*).

Note that the detection of the macro defect 14*a*(*j*) and the creation of the macro defect map 15(*j*) are performed in sequence for each of all of the wafers 14(*l*) to 14(*n*) in the cassette 16 that is transferred to the automatic inspection apparatus 11 (100% inspection). Then, obtained macro defect maps 15(*l*) to 15(*n*) are outputted together with he cassette 16's numbers and the numbers of the tiers in the cassette 16 in which the wafers 14(*l*) to 14(*n*) are stored. They are outputted to the inspection data storage unit 12.

Next, the inspection data storage unit 12 will be explained. The inspection data storage unit 12 is a data server that acquires the macro defect maps 15(*l*) to 15(*n*), the cassette 16's number, and the numbers of the tiers in the cassette 16 outputted from the automatic macro inspection apparatus 11 via not-shown communication means, and assigns appropriate ID numbers to the macro defect maps 15(*l*) to 15(*n*) for storage. The ID numbers are referred to when the macro defect maps 15(*l*) to 15(*n*) are identified by the cassette 16's number and the numbers of the tiers in the cassette 16.

Thus, the inspection data storage unit 12 stores therein the macro defect maps 15(*l*) to 15(*n*) for the wafers 14(*l*) to 14(*n*), while the automatic macro inspection apparatus 11 executes the macro inspection on the wafers 14(*l*) to 14(*n*) which are housed in the cassette 16 and thereafter transferred to the overlay measurement apparatus 13. Then, the overlay measurement apparatus 13 executes the overlay inspection on the wafers 14(*l*) to 14(*n*).

After selecting a wafer 14(*j*) suitable for the overlay inspection from the wafers 14(*l*) to 14(*n*) housed in the cassette 16 by a later-described method, the overlay measurement apparatus 13 illuminates a very small region of the wafer 14(*j*) and captures the image of the wafer 14(*j*) from the reflected light and so on generated from the wafer 14(*j*). Then, the overlay measurement apparatus 13 subjects the obtained wafer image to the image processing to automatically measure a relative offset (overlay offset) between the resist pattern formed on the surface of the wafer 14(*j*) and an underlying pattern.

Figure 3A:
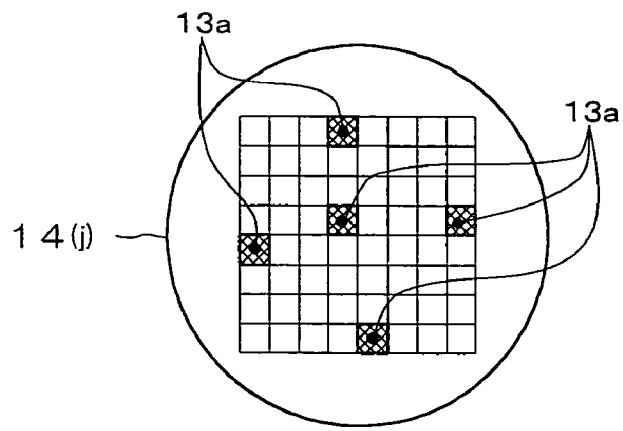

Inspection accuracy of the overlay measurement apparatus 13 is 100 nm to 10 nm or less, and an inspection area ratio of the overlay measurement apparatus 13 is about $10^{-8}$%. A plurality of sampling regions 13*a* (FIG. 3A) are empirically prepared in advance for inspection regions of the wafer 14(*j*) in conformity with this inspection area ratio. The sampling regions 13*a* correspond to a predetermined portion in the claims.

The kind of the defect (anomaly in overlay offset of the resist pattern) detected by the overlay measurement apparatus 13 is microscopic and invisible to the human eye. Further, the kind of the defect (the anomaly in overlay offset of the resist pattern) is not associated with the kind of the aforesaid macro defect 14*a*(*j*) (a foreign particle, a scratch of the resist pattern, or the like) detected by the automatic macro inspection apparatus 11. This means that the macro defect 14*a*(*j*) never directly affects variation in overlay offset.

However, if the macro defect 14*a*(*j*) is present in the regions (the sampling regions 13*a* of the wafer 14(*j*)) inspected by the overlay measurement apparatus 13 (see FIG. 3B), it causes some change in the measurement results of the overlay measurement apparatus 13 or causes difficulties in normal overlay measurement.

In order to avoid such a situation, the overlay measurement apparatus 13 executes processings in FIG. 4 (Steps S10 to S16) in sequence to select the wafer 14(*j*) suitable for the overlay inspection from the wafers 14(*l*) to 14(*n*) housed in the cassette 16, and then executes the overlay inspection on the sampling regions 13*a* (FIG. 3A) of the wafer 14(*j*).

Specific operations of the overlay measurement apparatus 13 will be described with reference to FIG. 4.

At Step S10, the overlay measurement apparatus 13 designates, as a first object to be processed, the wafer 14(*l*) placed on the first tier from the wafers 14(*l*) to 14(*n*) in the transferred cassette 16, and executes processings of subsequent Steps S11 to S14 thereon.

At Step S11, with reference to the ID numbers of the wafer defect maps stored in the inspection data storage unit 12, the overlay measurement apparatus 13 identifies the macro defect map 15(*l*) corresponding to the wafer 14(*l*) from the cassette 16's number containing the wafer 14(*l*) and the number of the tier, and acquires the identified macro defect map 15(*l*) via the not-shown communication means.

Figure 2:
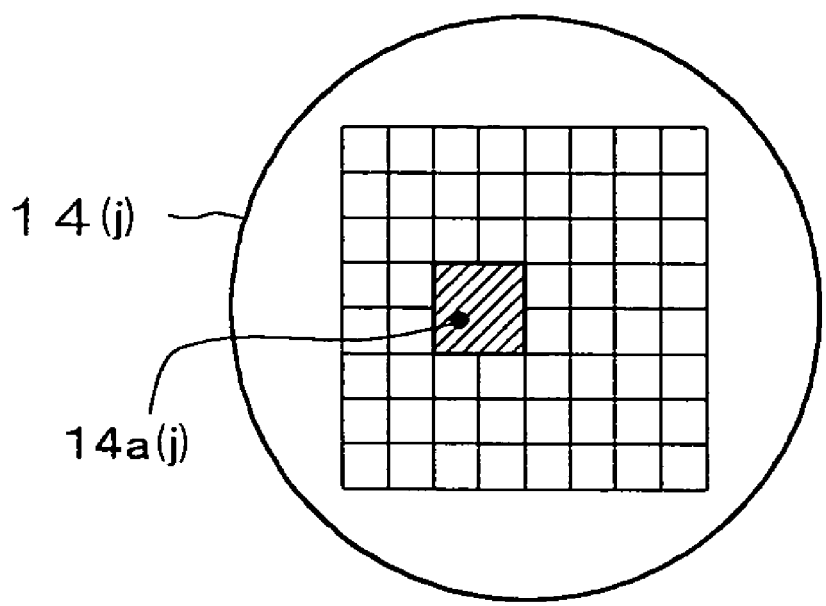
FIG. 2 illustrates a macro defect 14a(j) on a wafer 14(j)

At Step S12, with reference to the acquired macro defect map 15(*l*), it judges whether or not the wafer 14(*l*) has a macro defect (see 14*a*(*j*) in FIG. 2). Then, with a negative judgment (No at S12), the flow goes to Step S13, the overlay measurement apparatus 13 extracts the wafer 14(*l*) corresponding to the macro defect map 15(*l*) from the top tier in the cassette 16 and executes the overlay inspection on the sampling regions 13*a* of the wafer 14(*l*) (see FIG. 3A) prepared in advance.

Further, with a positive judgment (Yes at S12), the flow goes to Step S14, where the overlay measurement apparatus 13 judges whether or not a region in which the macro defect is distributed overlaps any of the sampling regions 13*a*. Then, if the judgment result is completely negative (No at S14), the flow goes to Step S13 where the overlay measurement apparatus 13 executes the overlay inspection on the sampling regions 13*a* (see FIG. 3C) of the wafer 14(*l*), similarly to the above.

Figure 3B:
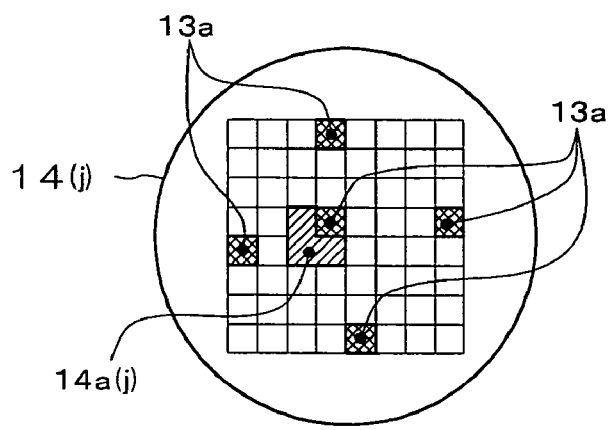
Figure 3C:
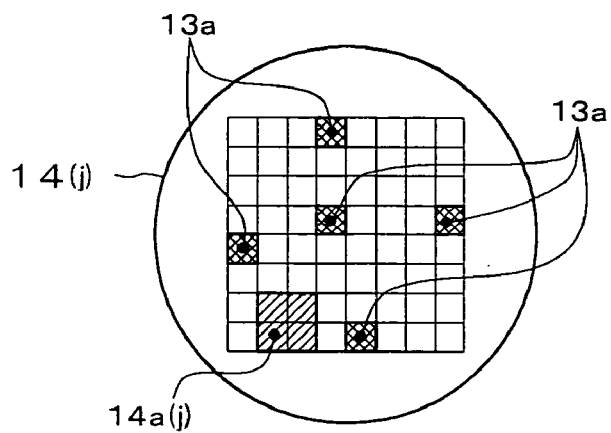

On the other hand, if the region in which the macro defect (see 14*a*(*j*)) is distributed overlaps at least part of the sampling regions 13*a* (Yes at S14) as shown in FIG. 3B, the overlay inspection on the sampling regions 13*a* of the wafer 14(*l*) does not produce an accurate result. Therefore, the overlay measurement apparatus 13 skips the overlay inspection and goes to the next Step S15.

At Step S15, it judges whether or not the total number of the wafers that have undergone the overlay inspection (i.e., Step S13) reaches a predetermined number m (m<n). The number of the wafers housed in the cassette 16 is n, and the number m of the wafers to undergo the overlay inspection is preset to a value smaller than the total number n. That is, the overlay inspection is generally executed for part of the wafers in the cassette 16 (spot inspection). Note that the wafer to undergo the overlay inspection is a wafer having no macro defects distributed in the sampling regions 13*a*.

With a judgment result of Step S15, the total number of the inspected wafers is smaller than the predetermined number m (No at S15), the overlay measurement apparatus 13 performs Step S16 and returns to Step S11. Then, it designates the wafer 14(2) placed on the second tier from the top of the cassette 16 as the second object to be processed, and subjects the wafer 14(2) to the same processings (Steps S11 to S15) as described above.

Steps S11 to S16 are repeated with wafers replaced until the judgment result of Step S15 shows that the total number of the inspected wafers has reached the predetermined number m (Yes at S15). Then, the total number of the inspected wafers reaching the predetermined number m completes the overlay inspection for the cassette 16.

After completion of the overlay measurement process as above, each cassette 16 is judged from the results of the above-described macro inspection and overlay inspection. Then, for example, when judged as normal the cassette 16 is sent to a subsequent process (a working process), when judged as defective the cassette 16 is sent to a reworking step, and when judged as nonreworkable the cassette 16 is discarded.

As described above, in the substrate inspection system 10 of the first embodiment, the overlay measurement apparatus 13 does not execute the inspection on the region having the macro defect 14*a*(*j*) detected by the automatic macro inspection apparatus 11. Therefore, it is possible to exclude the region in which the macro defect 14*a*(*j*) is distributed, from objects of the inspection by the overlay measurement apparatus 13.

Consequently, it is possible to constantly measure the overlay offset of the resist pattern with accuracy without being affected by a foreign particle adhering to the surface of the wafer 14(*j*), a scratch on the resist pattern, or the like (the macro defect 14*a*(*j*)). Accordingly, an anomaly in overlay offset of the resist pattern can also be accurately detected, resulting in improving inspection reliability.

Further, selecting suitable inspection regions (the sampling regions 13*a*) for the overlay inspection on a wafer basis in the cassette 16 makes avoidable unnecessary execution of the overlay inspection on the region having the macro defect 14*a*(*j*) distributed therein, therefore, the overlay measurement apparatus 13 can efficiently execute the inspection with accuracy.

Further, for use of the inspection of the overlay measurement apparatus 13 as monitoring over-time variation in the manufacturing process, it is also possible to perform accurate and efficient process monitoring without any influence given from an accidental defect (a singular point of the process variation being excluded) even if the accidental defect in no direct association with process variation (variation in the overlay offset) monitored by the overlay measurement apparatus 13 occurs.

The above-described first embodiment has described the example where the automatic macro inspection apparatus 11 outputs the macro defect map 15(*j*) relating to the information on distribution of the macro defect 14*a*(*j*), and the overlay measurement apparatus 13 refers to the macro defect map (*j*) before the overlay inspection, but the present invention is not limited thereto.

For example, it may be configured that the automatic macro inspection apparatus 11 outputs information on present/absence of the macro defect 14(*j*), the inspection data storage unit 12 stores the presence/absence information, and the overlay measurement apparatus 13 refers to the presence/absence information before the execution of the overlay inspection. The overlay measurement apparatus 13 in this case operates by the steps without Step S14 of FIG. 4. Therefore, it executes the overlay inspection only on the wafer 14(*j*) in which no macro defect 14(*j*) is distributed, out of the wafers 14(*l*) to 14(*n*) in the cassette 16.

Further, the above-described first embodiment has described the example of the substrate inspection system 10 using the overlay measurement apparatus 13, but the present invention is not limited thereto. Any inspection apparatus can replace the overlay measurement apparatus 13 as long as it is capable of detecting defects not associated with the kind of the macro defect 14*a* detected by the automatic macro inspection apparatus 11. The same effects as those described above are also obtained in this case.

Second Embodiment

As shown in FIG. 5, a substrate inspection system 30 of a second embodiment has an automatic macro inspection apparatus 31 (a first inspection apparatus) in place of the above-described automatic macro inspection apparatus 11 and a line width measurement apparatus 33 (a second inspection apparatus) in place of the above-described overlay measurement apparatus 13. The substrate inspection system 30 executes a macro inspection and a line width inspection on wafers 14(*l*) to 14(*n*) in the cassette 16 in sequence. The line width inspection is made on a small region. The basic configuration of the automatic macro inspection apparatus 31 is the same as that of the above-described automatic macro inspection apparatus 11.

Figure 6:
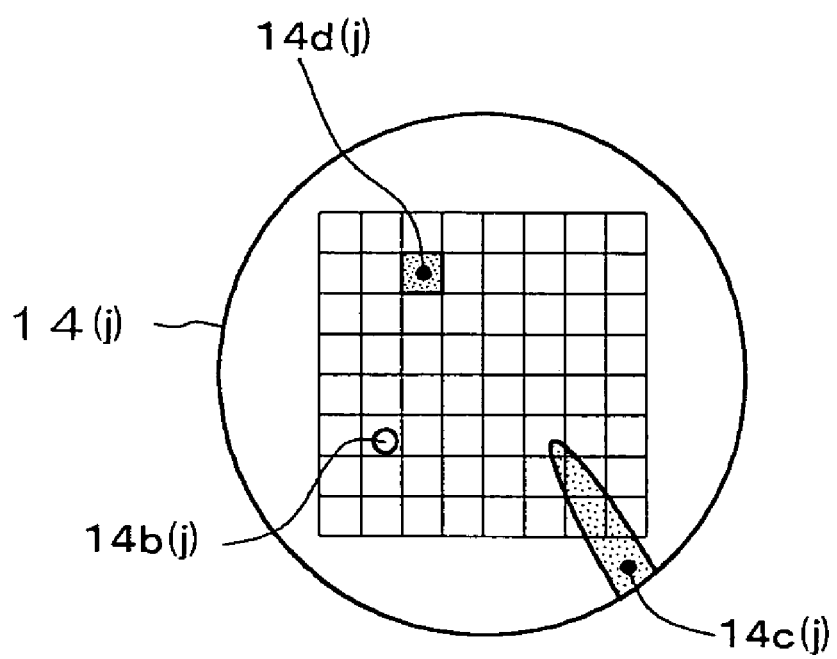
FIG. 6 illustrates automatic classification of macro defects on a wafer 14.

When automatically detecting macro defects 14b(j) to 14d(j) on a wafer 14(j) (FIG. 6) similarly to the above-described automatic macro inspection apparatus 11, the automatic macro inspection apparatus 31 also automatically classifies the macro defects 14b(j) to 14d(j) based on pattern characteristics and light intensities of a wafer image.

For example, a foreign particle adhering to a surface of the wafer 14(j) (the macro defect 14b(j)) appear as a shining small point on the wafer image. Unevenness of coating on a resist layer (the macro defect 14c(j)) appears as a comet shape trailing outward from the center on the wafer image. Unevenness of thickness and anomaly in cross-sectional shape due to defocus at the time of exposure (the macro defect 14d(j)) appear different, bright or dark on every shot of the wafer image.

Thus, the macro defects 14b(j) to 14d(j) of the wafer 14(j) show different pattern characteristics and light intensities on the wafer image depending on what kind of defects they are, so that automatic defect classification is made possible by storing these characteristics and so on in the automatic macro inspection apparatus 31 in advance and referring to them for detecting the macro defects 14b(j) to 14d(j).

Then, the automatic macro inspection apparatus 31 automatically converts distribution information and classification information of the macro defects 14b(j) to 14d(j) detected from the wafer 14(j) to electronic information to create a macro defect map 35(j), and it automatically outputs this macro defect map 35(j). The macro defect map 35(j) contains information on the position coordinates and areas of the detected macro defects 14b(j) to 14d(j) on the wafer 14(j) and on the kinds of the defects.

The detection and classification of the macro defects 14b(j) to 14d(j) and the creation of the macro defect map 35(j) are performed in sequence for each of all the wafers 14(l) to 14(n) in the cassette 16 transferred to the automatic macro inspection apparatus 31 (100% inspection).

Then, it outputs the obtained macro defect maps 35(l) to 35(n) together with the cassette 16's number housing the wafers 14(l) to 14(n) and the numbers of tiers in the cassette 16, and the inspection data storage unit 12 acquires them via a not-shown communication means. The macro defect maps 35(l) to 35(n) are assigned respective appropriate ID numbers in the inspection data storage unit 12.

Meanwhile, after the automatic macro inspection apparatus 31 completes the macro inspection on the wafers 14(l) to 14(n), the wafers 14(l) to 14(n) housed in the cassette 16 are transferred to the line width measurement apparatus 33. Then, the line width measurement apparatus 33 executes a line width inspection on the wafers 14(l) to 14(n).

After selecting a wafer 14(j) suitable for the line width inspection from the wafers 14(l) to 14(n) in the cassette 16 by a later-described method, the line width measurement apparatus 33 illuminates a very small region of the wafer 14(j) and captures an image of the wafer 14(j) according to reflected light and so on generated from the wafer 14(j). Then, it performs image processing on the obtained wafer image so as to automatically measure a line width of a resist pattern formed on a surface of the wafer 14(j). Inspection accuracy of the line width measurement apparatus 33 is 100 nm to 10 nm or less. An inspection area ratio of the line width measurement apparatus 33 is about $10^{-8}$%.

The kinds of defects (anomaly in line width of the resist pattern) detectable by the line width measurement apparatus 33 are microscopic and invisible to the human eye. Also, the kinds of the defects (anomaly in line width of the resist pattern) are associated with the kinds of the above-described macro defects 14b(j) to 14d(j) detected by the automatic macro inspection apparatus 31, and in particular, they are closely associated with unevenness of thickness and anomaly in cross-sectional shape (the macro defect 14d(j)) due to defocus at the time of exposure. That is, the macro defect 14d(j) due to defocus may be in direct association with the anomaly in line width of the resist pattern.

Therefore, the line width measurement apparatus 33 executes processings (Steps S30 to S36) in FIG. 7 in sequence to select the wafer 14(j) suitable for the line width inspection from the wafers 14(l) to 14(n) in the cassette 16, and thereafter executes the line width inspection on the wafer 14(j). Steps S30 to S32, S35, and S36 in FIG. 7 are the same as Steps S10 to S12, S15, and S16 in FIG. 4 described above, and therefore detailed description thereof will be omitted.

The line width measurement apparatus 33 acquires a wafer defect map 35(i) from the inspection data storage unit 12 (S31), judges if the macro defects 14b(i) to 14d(i) are present or absent (S32). With a presence of the macro defect 14d(i) (Yes at S32), the flow goes to Step S33 where it is determined whether or not the macro defect 14d(i) is one due to defocus at the time of exposure.

When it is judged that there is the macro defect 14d(i) due to defocus (Yes at S33), the flow goes to Step S34 where a wafer 14(i) corresponding to the wafer defect map 35(i) is extracted from the cassette 16 to execute the line width inspection on a region (see FIG. 6) in which the macro defect 14d(i) due to defocus is distributed. In the second embodiment, the region having distributed therein the macro defect 14d(i) corresponds to a predetermined portion in the claims.

On the other hand, with no the macro defects (14b to 14d) on the wafer 14(i) (No at S32), or if the macro defect 14d(i) due to defocus is not present (No at S33), the line width measurement apparatus 33 skips Step S34 and goes to the next Step S35 (in other words, without the line width inspection on the wafer 14(i)).

At Step S35, it judges whether or not the total number of the wafers after the line width inspection (i.e., after Step S34) has reached a predetermined number k (k<n). The number of wafers housed in the cassette 16 is n, but the number k of wafers to undergo line width inspection is set to be a smaller value than the total number n (spot inspection). Note that which wafer is to undergo line width inspection is determined with reference to the wafer defect map 35(i).

Steps S31 to S36 are repeated with wafers being replaced, until as a judgment result of Step S35 the total number of the inspected wafers has reached the predetermined number k (Yes at Step S35). Then, the total number of the inspected wafers reaching the predetermined number k completes the line width inspection for the cassette 16.

After completion of the line width measurement process as above, every cassette 16 is judged based on the results of the above-described macro inspection and line width inspection. Then, for example, when judged as normal the cassette 16 is sent to a subsequent process (a working process), when judged as defective the cassette 16 is sent to a reworking process, and when judged as nonreworkable the cassette 16 is discarded.

As described above, the substrate inspection system 30 of the second embodiment decides a wafer to undergo the line width inspection, with reference to the kind of the macro defect detected by the automatic macro inspection apparatus 31. Specifically, it determines a wafer having a macro defect (for example, the macro defect 14d due to defocus at the time of exposure) closely associated with the kind of the defect detectable by the line width measurement apparatus 33 (the anomaly in line width of the resist pattern) as the wafer to undergo the line width inspection.

Consequently, it is possible to execute the line width inspection efficiently on a shot in which the macro defect 14d due to defocus is detected. Further, detailed line width measurement of the macro defect 14d due to defocus is made possible, so that it is also possible to obtain a quantitative idea of how many nm the line width of the resist pattern has changed from a normal value due to defocus. Moreover, it is possible to detect defects (the anomaly in line width) that are not detectable through the line width measurement in preset sampling regions, which improves inspection reliability.

Note that in addition to the line width inspection on the shot in which the macro defect 14d due to defocus is detected, the line width inspection may also be executed on a plurality of sampling regions 13a (FIG. 3A) prepared in advance. However, in a case where there is the macro defect 14b (a foreign particle) or the macro defect 14c (unevenness of resist coating) that are not closely associated with the defect (the anomaly in line width) detectable by the line width measurement apparatus 33 in the sampling region 13a, it is preferable not to execute the line width inspection on this sampling region 13a. This realizes efficient line width inspection.

Further, for use of inspection of the line width measurement apparatus 33 as process monitor, efficient process monitoring is made possible without affected from an accidental defect (the singular point of the process variation being excluded), which is in no direct association with process variation (variation in the line width of the resist pattern) monitored by the line width measurement apparatus 33.

Moreover, the above-described second embodiment has described the substrate inspection system 30 using the line width measurement apparatus 33, but the present invention is not limited thereto. Any inspection apparatus is usable in place of the line width measurement apparatus 33 as long as it is capable of detecting defects associated with the kinds of the macro defects (14b to 14d) detected by the automatic macro inspection apparatus 31. The same effects as those described above are also obtained in this case.

For example, with use of a cross-sectional shape measurement apparatus to measure the cross sectional shapes of a resist pattern in place of the above-described line width measurement apparatus 33, the cross-sectional shape measurement apparatus is detectable of kinds of defects (anomaly in cross-sectional shape) which are closely associated with the macro defect 14d due to defocus at the time of exposure, and therefore, it may execute cross-sectional shape measurement of the region in which the macro defect 14d is distributed. This enables the measurement of the detailed cross-sectional shapes of the macro defect 14d due to defocus, which makes it possible to know how the cross sectional shapes of the resist pattern have changed due to defocus.

In addition, with use of a thickness measurement apparatus to measure the resist layer thickness in place of the above-described line width measurement apparatus 33, this thickness measurement apparatus is detectable of the kinds of defects (anomaly in thickness) which are closely associated with unevenness of coating on a resist layer (the macro defect 14c) and the macro defect 14d due to defocus, and therefore, it may execute thickness measurement of the regions having these macro defects 14c, 14d distributed therein. This enables detailed thickness measurement of the unevenness of coating on the resist layer (14c) and the macro defect 14d due to defocus, which also makes it possible to know how many nm the thickness has changed relative to a preferable thickness.

Moreover, with use of a surface foreign particle inspection apparatus to inspect a foreign particle on a substrate surface in place of the above-described line width measurement apparatus 33, this surface foreign particle inspection apparatus is detectable of the kinds of defects (foreign particles) which are closely associated with foreign particles adhering to the surface of the wafer 14 (the macro defect 14b), and therefore, it may execute foreign particle inspection on the region having the macro defect 14b distributed therein. This makes it possible to specify substances constituting the foreign particles and to know how many μm the size thereof is.

Further, the line width measurement apparatus 33, the cross-sectional shape measurement apparatus, the thickness measurement apparatus, and the surface foreign particle inspection apparatus can be used in combination. In this case, it is able to efficiently execute the line width inspection, cross-sectional shape inspection, thickness inspection, and foreign particle inspection according to the kind of the defects by automatically classifying defects (foreign particle, coating defect, and defocus) detected by the automatic macro inspection apparatus 31.

In addition, the overlay measurement apparatus 13 described in the first embodiment can also be combined with the line width measurement apparatus 33 and the cross-sectional shape measurement apparatus described in the second embodiment. Besides, it may be combined with a microscope apparatus, a pattern defect inspection apparatus to inspect a pattern defect, and a flatness measurement apparatus to measure a planar shape of a substrate. As the microscope apparatus, usable is, for example, an optical microscope, an electron microscope, an atomic force microscope, a near field optical microscope, or the like.

In a substrate inspection system having the plural inspection apparatuses (13, 33, . . . ) in combination, the inspection data storage unit 12 stores therein distribution information and classification information (a macro defect map) of macro defects detected by the automatic macro inspection apparatus to share the macro defect map by the plural inspection apparatuses (13, 33, . . . ), which realizes various kinds of efficient inspections.

Further, the above-described embodiments have described the example of inspecting the wafers for IC manufacturing in the manufacturing process of semiconductor circuit elements, but the present invention is similarly applicable to inspection of glass substrates for liquid crystal manufacturing in the manufacturing process of liquid crystal display elements.

In the above-described embodiments, the inspection data storage unit 12 is a data server, and is installed outside the automatic macro inspection apparatus 11, the overlay measurement apparatus 13, and the line width measurement apparatus 33, but storage units installed inside the respective measurement inspection apparatuses may be used. It may be configured that data are stored in a storage unit in at least one measurement inspection apparatus and the data are readable/writable from/to other inspection apparatuses.

As has been explained above, the above-described embodiments make it possible to realize efficient operation of inspecting both of a large region and a small region of a substrate and highly reliable inspection without increasing costs.

What is claimed is:

1. A substrate inspection system comprising:
a first inspection apparatus executing a macro inspection of each of a plurality of substrates and outputting information on a defect on each of the substrates;
a storage unit storing therein for each of the substrates the information on a defect outputted from said first inspection apparatus; and
a second inspection apparatus to execute an inspection of a predetermined portion of the substrates, the predetermined portion set in advance of the macro inspection, wherein
said second inspection apparatus refers to the information on a defect stored in said storage unit and determines which of the substrates or which regions of the substrates are to be inspected from amongst the plurality of substrates, the regions including the predetermined portion of the substrates.

2. The substrate inspection system according to claim 1, wherein:
the information on the defect obtained by the first inspection apparatus is information on presence/absence of a defect on each of the substrates, and
the second inspection apparatus refers to the information on presence/absence of a defect and executes the inspection of the substrates or of the regions of the substrates based on whether or not the substrates or the regions have the defect.

3. The substrate inspection system according to claim 1, wherein:
the information on the defect obtained by the first inspection apparatus is information on distribution of the defect on each of the substrates, and
the second inspection apparatus refers to the information on distribution of a defect and executes the inspection of the substrates or of the regions of the substrates based on whether or not the substrates or regions have the defect distributed in the predetermined portion of the substrates.

4. The substrate inspection system according to claim 1, wherein:
the information on the defect obtained by the first inspection apparatus is information on distribution and classification of the defect on each of the substrates, and
the second inspection apparatus refers to the information on distribution and classification of the defect and executes the inspection of the substrates or of the regions of the substrates based on the stored distribution and classification of the defect for each of the substrates.

5. The substrate inspection system according to claim 1, wherein:
said second inspection apparatus executes the inspection by measuring a relative offset between a resist pattern formed on a surface of the substrate and an underlying pattern.

6. The substrate inspection system according to claim 1, wherein:
said second inspection apparatus executes the inspection by measuring a line width of a resist pattern formed on a surface of the substrate.

* * * * *